(12) United States Patent
Ohto

(10) Patent No.: US 9,086,384 B2
(45) Date of Patent: Jul. 21, 2015

(54) SHAPE MEASURING DEVICE, SHAPE MEASURING METHOD, AND GLASS PLATE MANUFACTURING METHOD

(71) Applicant: ASAHI GLASS COMPANY, LIMITED, Tokyo (JP)

(72) Inventor: Kimiaki Ohto, Tokyo (JP)

(73) Assignee: ASAHI GLASS COMPANY, LIMITED, TOKYO (JP)

( * ) Notice: Subject to any disclaimer, the term of this patent is extended or adjusted under 35 U.S.C. 154(b) by 190 days.

(21) Appl. No.: 13/714,836

(22) Filed: Dec. 14, 2012

(65) Prior Publication Data

US 2013/0098109 A1  Apr. 25, 2013

Related U.S. Application Data

(63) Continuation of application No. PCT/JP2011/063712, filed on Jun. 15, 2011.

(30) Foreign Application Priority Data

Jun. 15, 2010  (JP) ................................. 2010-136510

(51) Int. Cl.
G01N 21/84 (2006.01)
G01B 11/00 (2006.01)
(Continued)

(52) U.S. Cl.
CPC ................ *G01N 21/84* (2013.01); *C03B 25/08* (2013.01); *G01B 11/24* (2013.01); *G01B 11/25* (2013.01); *G01N 21/896* (2013.01); *H04N 7/18* (2013.01); *G01N 2021/8965* (2013.01)

(58) Field of Classification Search
CPC ................ G01N 21/84; G01N 21/896; G01N 2021/8965; G03B 25/08; G01B 11/24; G01B 11/25
See application file for complete search history.

(56) References Cited

U.S. PATENT DOCUMENTS

| 2,253,054 A | 8/1941 | Tuttle et al. |
| 2,816,474 A | 12/1957 | Powell |

(Continued)

FOREIGN PATENT DOCUMENTS

| EP | 1 750 087 A1 | 2/2007 |
| JP | 51-12155 | 1/1976 |

(Continued)

OTHER PUBLICATIONS

International Search Report PCT/JP2011/063712 dated Jul. 26, 2011.

(Continued)

*Primary Examiner* — Jodi C Franklin
(74) *Attorney, Agent, or Firm* — Foley & Lardner LLP

(57) ABSTRACT

A shape measuring apparatus includes: an image pick-up section that captures an image of two reflection spot groups of a pattern reflected in a first surface M1 and a second surface of a transparent flat plate and generates an image containing two reflection images separated in a direction perpendicular to a direction of extending; a first surface reflection spot group estimating section that estimates from the image a first surface reflection spot group of the pattern generated by the first surface of the transparent flat plate; an inclination angle calculating section that calculates an inclination angle of the first surface of the transparent flat plate at an estimated position of the first surface reflection spot group; and a surface shape determining section that determines a shape of the first surface of the transparent flat plate based on the calculated inclination angle.

8 Claims, 9 Drawing Sheets

(51) Int. Cl.
  *C03B 25/08*  (2006.01)
  *G01B 11/24*  (2006.01)
  *H04N 7/18*  (2006.01)
  *G01B 11/25*  (2006.01)
  *G01N 21/896*  (2006.01)

(56) References Cited

U.S. PATENT DOCUMENTS

| | | | |
|---|---|---|---|
| 5,210,592 | A | 5/1993 | Bretschneider |
| 5,298,974 | A | 3/1994 | Chandley |
| 5,309,222 | A | 5/1994 | Kamei et al. |
| 5,880,843 | A | 3/1999 | Hermosillo-Valadez et al. |
| 6,392,754 | B1 * | 5/2002 | Pingel et al. .......... 356/603 |
| 7,394,536 | B2 | 7/2008 | Sonda et al. |
| 2007/0091319 | A1 | 4/2007 | Sonda et al. |
| 2008/0225303 | A1 | 9/2008 | Lampalzer |
| 2009/0195774 | A1 | 8/2009 | Kawakami |
| 2010/0060905 | A1 | 3/2010 | Wienand |

FOREIGN PATENT DOCUMENTS

| | | |
|---|---|---|
| JP | 55-140102 | 11/1980 |
| JP | 03-276005 | 12/1991 |
| JP | 07-128032 | 5/1995 |
| JP | H08-304054 A | 11/1996 |
| JP | H10-185534 A | 7/1998 |
| JP | 11-148813 | 6/1999 |
| JP | 2001-502800 | 2/2001 |
| JP | 2001-249010 | 9/2001 |
| JP | 2003-192361 | 7/2003 |
| JP | 2005-345383 A | 12/2005 |
| JP | 2009-128098 | 6/2009 |
| JP | 2009-139355 A | 6/2009 |
| WO | WO-2009/102490 A1 | 8/2009 |

OTHER PUBLICATIONS

Extended European Search Report dated Aug. 27, 2014 issued in Application No. 11795773.8.

Skydan O.A., et al., "3D shape measurement of automotive glass by using a fringe reflection technique," Measurement Science and Technology, vol. 18, No. 1, Nov. 30, 2006, pp. 106-114.

\* cited by examiner

FIG. 6
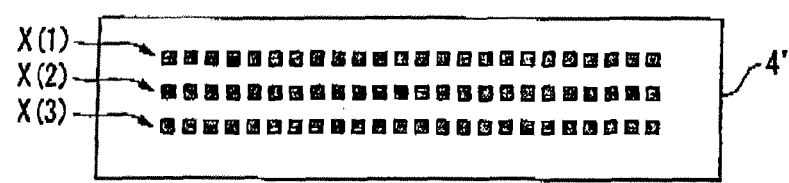
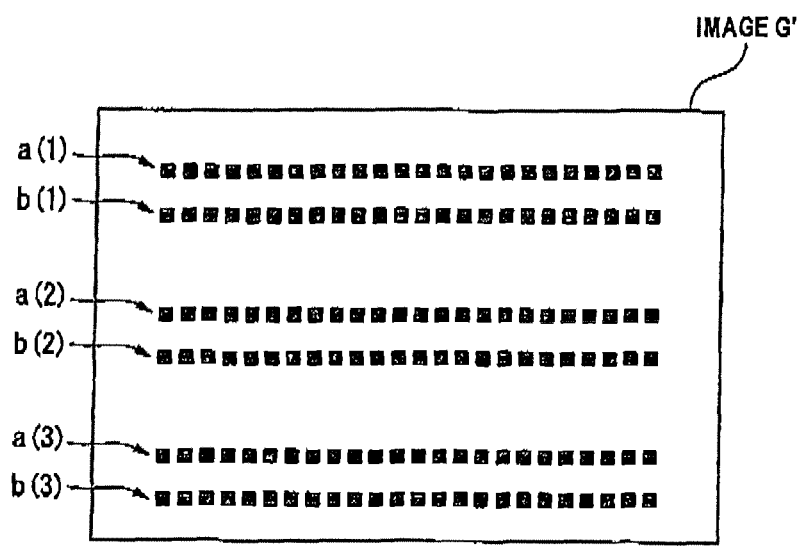

400 # SHAPE MEASURING DEVICE, SHAPE MEASURING METHOD, AND GLASS PLATE MANUFACTURING METHOD

TECHNICAL FIELD

The present invention relates to a shape measuring apparatus, a shape measuring method, and a manufacturing method for glass plates.

BACKGROUND ART

In the conventional art, as an example of a method of measuring a surface shape such as fine waviness in the first surface of a transparent flat plate, a technique disclosed in JP-A-2009-128098 is known. In this measuring method, an image generated when a pattern arranged above a transparent flat plate is reflected in the first surface of the transparent flat plate is captured by a line sensor. Then, on the basis of the obtained image, the surface shape of the transparent flat plate is calculated.

SUMMARY OF THE INVENTION

Problem to be Solved by the Invention

Nevertheless, in the measuring method of JP-A-2009-128098, in order that the first surface reflection image and the second surface reflection image of the transparent flat plate should be separated so that an exact surface shape should be obtained, a pattern designed in correspondence to the plate thickness of the transparent flat plate and an image capturing means like a three-line type color camera constructed from a plurality of line sensors have been necessary. Further, when the measuring method of JP-A-2009-128098 is used, the first surface reflection image and the second surface reflection image can be separated. Nevertheless, it has been difficult to determine which one of these is the first surface reflection image.

The present invention has been devised in view of such situations. Its object is to allow a simple construction to achieve accurate measurement of the surface shape of a transparent flat plate.

Means for Solving the Problem

In order to resolve the above-mentioned problems, the shape measuring apparatus according to an aspect of the present invention includes: an image pick-up section that is arranged such that an optical axis becomes perpendicular to a direction of extending of a linear pattern arranged above a transparent flat plate serving as a measurement object, the image pick-up section being configured to capture an image of two reflection spot groups of the pattern generated by a first surface and a second surface of the transparent flat plate and generate an image containing two reflection images separated in a direction perpendicular to the direction of extending; a first surface reflection spot group estimating section configured to estimate a first surface reflection spot group of the pattern generated from the image by the first surface of the transparent flat plate by using a positional relation of the transparent flat plate, the pattern, and the image pick-up section; an inclination angle calculating section configured to calculate an inclination angle of the first surface of the transparent flat plate at a position of the estimated first surface reflection spot group by using the positional relation of the transparent flat plate, the pattern, and the image pick-up section; and a surface shape determining section configured to determine a shape of the first surface of the transparent flat plate based on the calculated inclination angle.

In the above-mentioned shape measuring apparatus, the inclination angle calculating section may calculate the inclination angle on the basis of a condition that an incident angle of incident light travelling from the pattern toward a position of the first surface reflection spot group is equal to a reflection angle of reflected light travelling from a position of the first surface reflection spot group toward the image pick-up section.

In the above-mentioned shape measuring apparatus, the pattern may be a pattern constructed such that a plurality of dots are arranged linearly in the extending direction.

In the above-mentioned shape measuring apparatus, the transparent flat plate may be conveyed in a direction perpendicular to the direction of extending.

In order to resolve the above-mentioned problems, the shape measuring method according to an aspect of the present invention includes the steps of: by using an image pick-up section arranged such that an optical axis becomes perpendicular to a direction of extending of a linear pattern arranged above a transparent flat plate serving as a measurement object, capturing an image of two reflection spot groups of the pattern generated by a first surface and a second surface of the transparent flat plate and thereby generates an image containing two reflection images separated in a direction perpendicular to the direction of extending; estimating from the image a first surface reflection spot group of the pattern in the first surface of the transparent flat plate by using a positional relation of the transparent flat plate, the pattern, and the image pick-up section; calculating an inclination angle of the first surface of the transparent flat plate at a position of the estimated first surface reflection spot group by using the positional relation of the transparent flat plate, the pattern, and the image pick-up section; and determining a shape of the first surface of the transparent flat plate based on the calculated inclination angle.

In the above-mentioned shape measuring method, the inclination angle calculating step may calculate the inclination angle on the basis of a condition that an incident angle of incident light travelling from the pattern toward the first surface reflection spot group is equal to a reflection angle of reflected light travelling from a position of the first surface reflection spot group toward the image pick-up section.

In the above-mentioned shape measuring method, the pattern may be a pattern constructed such that a plurality of dots are arranged linearly in the extending direction.

In the above-mentioned shape measuring method, the transparent flat plate may be conveyed in a direction perpendicular to the direction of extending.

In order to resolve the above-mentioned problems, the manufacturing method for glass plates according to an aspect of the present invention includes: a melting step of melting raw material so as to obtain molten glass; a forming step of forming the molten glass into a continuous plate-shaped glass ribbon; a slow cooling step of gradually cooling the glass ribbon in the course of conveying so as to remove stress; a measurement step of measuring the surface shape of the glass ribbon; a cutting step of cutting the glass ribbon; and a control step of controlling slow cooling conditions in the slow cooling step based on a measurement result of the measurement step, wherein the measurement step is a step in which measurement is performed on the glass ribbon by using the above-mentioned shape measuring method.

Effects of the Invention

According to the present invention, a simple construction is allowed to achieve accurate measurement of the surface shape of a transparent flat plate.

BRIEF DESCRIPTION OF THE DRAWINGS

FIG. 6 is a diagram showing a pattern provided in a pattern member 4' and an image G' captured by a camera 2 according to a second embodiment.

MODES FOR CARRYING OUT THE INVENTION

First Embodiment

A first embodiment of the present invention is described below with reference to the drawings.

Figure 1:
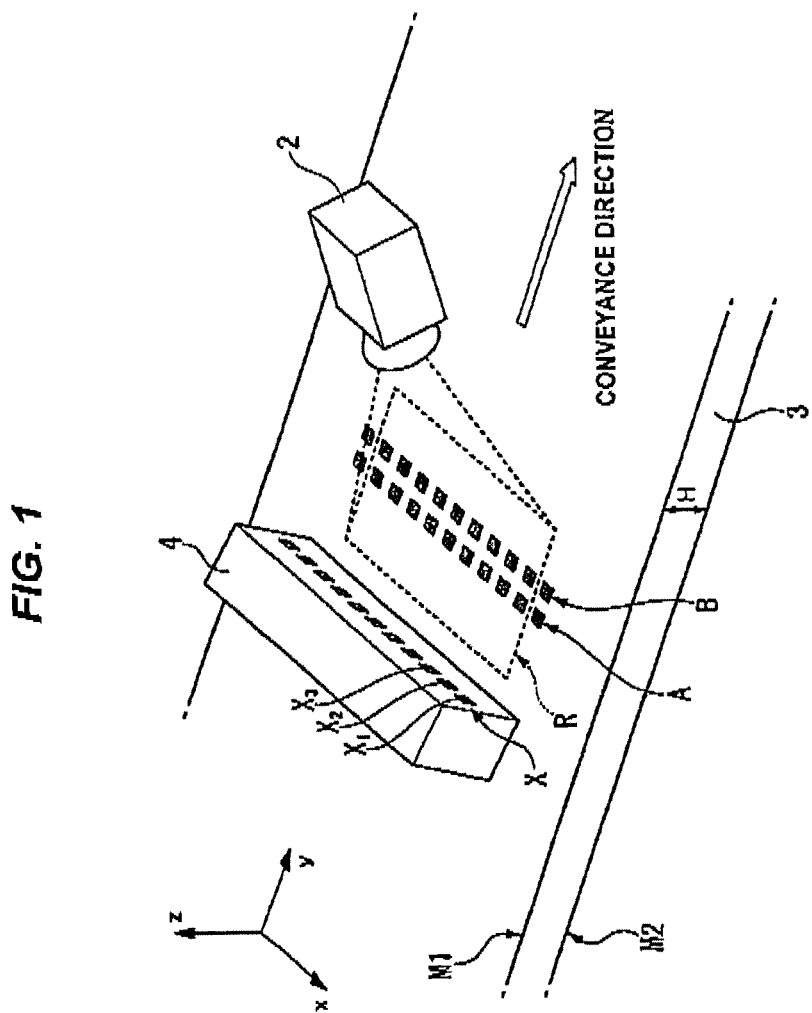
FIG. 1 is a diagram showing a measuring method for the surface shape of a transparent flat plate according to a first embodiment.

FIG. 1 is a diagram showing a measuring method for the surface shape of a transparent flat plate according to the first embodiment.

Figure 10:
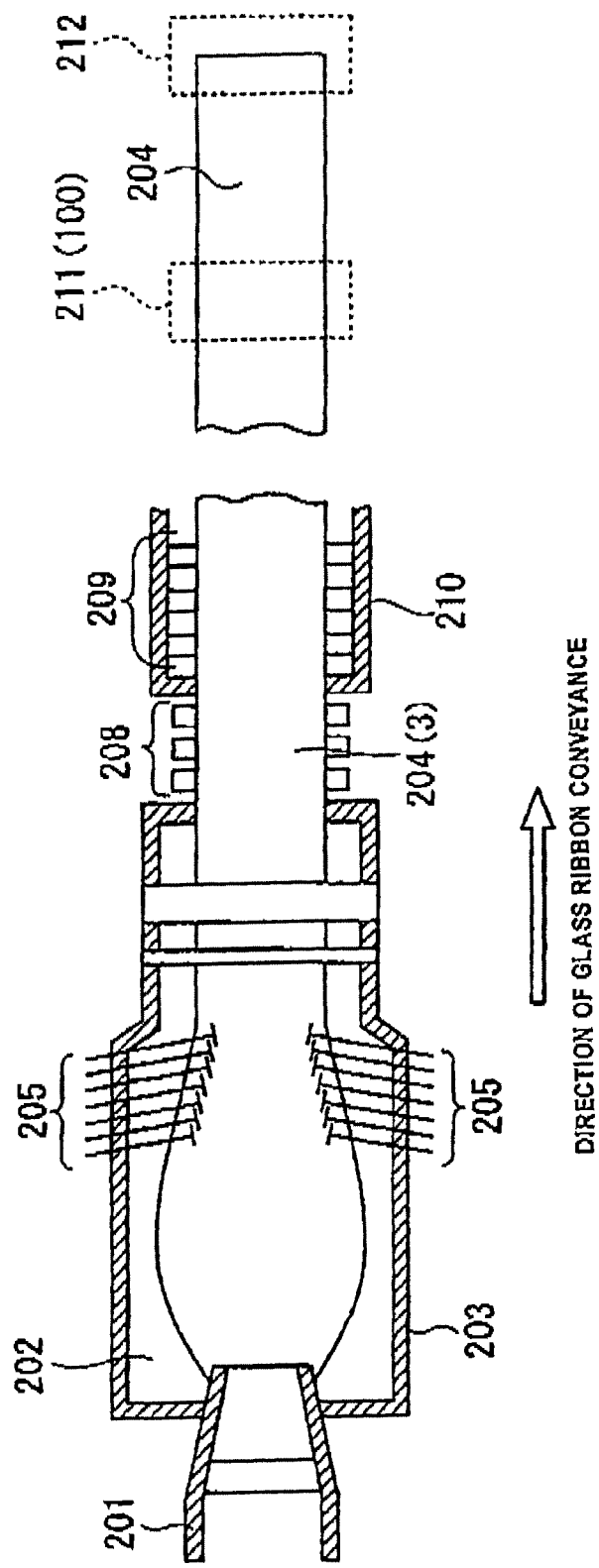
FIG. 10 is a schematic explanation diagram for a manufacturing line for glass plates where a shape measuring apparatus is employed.

A transparent flat plate 3 serving as a measurement object is, for example, a glass plate (a glass ribbon 204 in FIG. 10, described later). In FIG. 1, the transparent flat plate 3 is conveyed in the y-direction shown in the figure by the conveying apparatus not shown.

Above the transparent flat plate 3 (in the z-direction in the figure), a pattern member 4 is provided. On one surface of the pattern member 4, a pattern X is provided that is constructed from dots $X_1, X_2, X_3, \ldots$ aligned in line. The pattern member 4 is arranged such that the direction of alignment of the dots $X_1, X_2, X_2, \ldots$ is in parallel to the x-direction in the figure (a direction perpendicular to the conveyance direction and parallel to the first surface of the transparent flat plate 3) and that the surface provided with the pattern X is slightly inclined toward the transparent flat plate 3 side. Accordingly, on the first surface M1 of the transparent flat plate 3, a reflection spot group A of the pattern X is formed in a manner of extending in a direction perpendicular to the conveyance direction.

Further, a camera (area camera) 2 is provided above the transparent flat plate 3. The camera 2 is arranged such that its optical axis is oriented in the direction perpendicular to the direction of extending of the reflection spot group A and that the reflection image of the pattern is contained within the picked-up image. Here, the positions and the orientations of the pattern member 4 and the camera 2 are fixed.

In the present embodiment, an image containing the reflection image of the pattern X is captured by using the camera 2 arranged in this manner. Then, on the basis of the obtained image, the shape of the first surface M1 of the transparent flat plate 3 is measured. Here, in the present embodiment, it is assumed that the height H (the average height) of the transparent flat plate 3 first surface is known and that the surface shape to be measured is fine waviness or the like present in the first surface M1 of the transparent flat plate 3.

Figure 2:
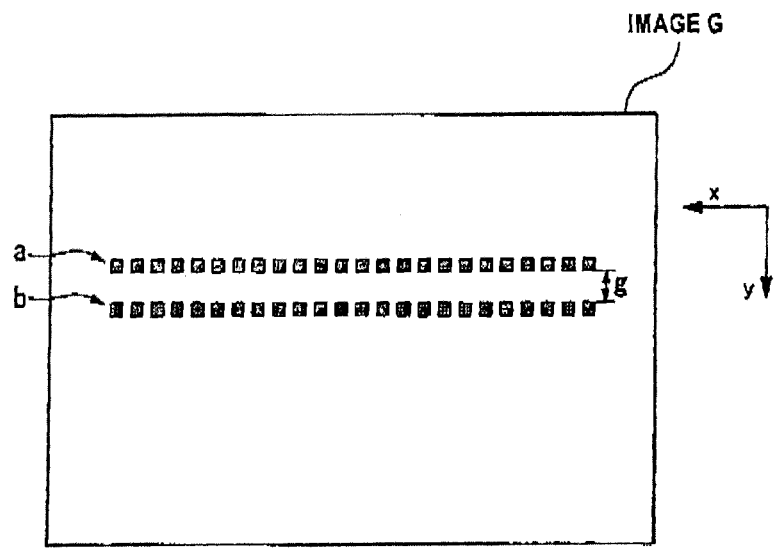
FIG. 2 is a diagram showing an example of an image G captured by a camera 2 according to a first embodiment.

Here, in the positional relation of the transparent flat plate 3, the pattern member 4, and the camera 2 shown in FIG. 1, the pattern X of the pattern member 4 is reflected in a reflection spot group B in the second surface M2 of the transparent flat plate 3, and then captured by the camera 2. FIG. 2 is a diagram showing an example of the image G captured by the camera 2. From the positional relation of the camera 2 in FIG. 1, the y-direction in FIG. 1 corresponds to the down direction in the image G in FIG. 2, and the x-direction in FIG. 1 corresponds to the left direction in the image G in FIG. 2. In the example in FIG. 1, as shown in FIG. 2, in the camera 2, the reflection image b generated by the reflection spot group B is captured in a state of being separated into a position deviating in the positive y-axis direction (toward the side close to the camera 2) from the reflection image "a" generated by the reflection spot group A in the first surface M1 of the transparent flat plate 3. The amount of positional deviation is determined by the position of arrangement of the pattern member 4 and the thickness t of the transparent flat plate 3. Then, when the size of each dot constituting the pattern X is sufficiently small, the line of the reflection image generated by the reflection spot group A is clearly separable from the line of the reflection image generated by the reflection spot group B.

Figure 3:
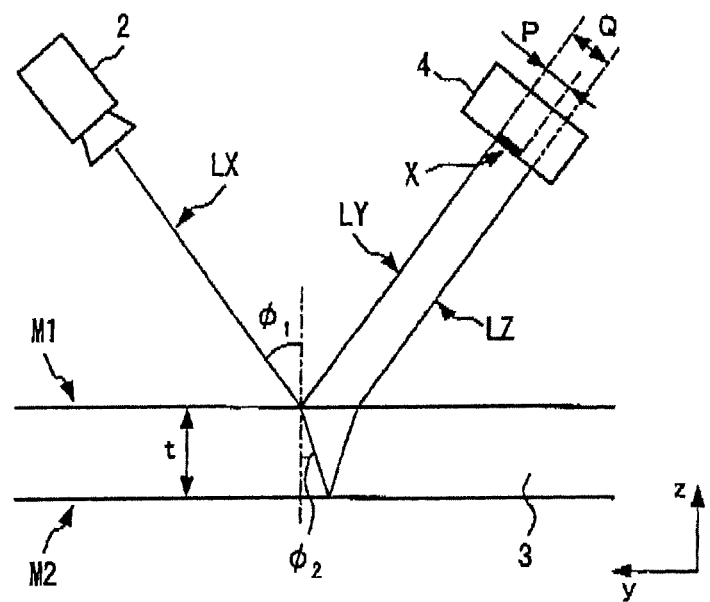
FIG. 3 is a diagram showing a light beam path in a case that a transparent flat plate 3 is image captured from a camera 2.

For example, the positional relation of the transparent flat plate 3, the pattern member 4, and the camera 2 and the size of each dot of the pattern X are determined by the relation shown in FIG. 3. FIG. 3 is a diagram showing the light beam path in a case that the transparent flat plate 3 is image-captured from the camera 2 in a situation viewed from the horizontal direction (the x-direction) in FIG. 1. The camera 2 and the pattern member 4 provided with the pattern X are arranged above the transparent flat plate 3 of plate thickness t. The length of each dot in the direction perpendicular to the direction of extending of the pattern X is P.

The following description is given for a case that reverse ray tracing is performed on the light beam reaching the camera 2, that is, for a case that the light beam path is traced from the camera side with a line of sight LX viewing the transparent flat plate 3 from the camera 2. FIG. 3 shows an example that the line of sight of the camera 2 (the straight line LX) is reflected in the first surface M1 of the transparent flat plate 3 at an angle equal to the incident angle $\phi_1$ and then travels in the direction of the light beam path LY so as to reach an edge of the pattern X. At that time, at the reflection spot in the first surface M1, the line of sight LX of the camera 2 is refracted into the transparent flat plate 3 at a refraction angle $\phi_2$, then reflected in the second surface M2, then refracted at the first surface M1, then travels in the direction of the light beam path LZ, and then reaches the pattern member 9. This indicates that the line of sight LX of the camera reaches two sites separated by a distance Q on the surface of the pattern member 4. That is, when a situation that the reflection images of the pattern X reflected in the front and the second surfaces of the transparent flat plate 3 are captured by the camera 2 is considered, it is indicated that the reflection image b generated by the reflection in the second surface M2 of the pattern X is generated at a position deviating by the distance Q from the reflection image "a" generated by the reflection in the first surface M1. Here, the distance Q is calculated according to the following Formula (1).

$$Q = 2t \cdot \cos \phi_1 \cdot \tan \phi_2 \quad (1)$$

Here, the incident angle $\phi_1$ and the refraction angle $\phi_2$ are in the relation of the following Formula (2), where the refractive index of the transparent flat plate 3 is denoted by n.

$$\sin \phi_1 = n \cdot \sin \phi_2 \quad (2)$$

In FIG. 2, the condition necessary for satisfying a requirement that the reflection images "a" and b generated by the reflection spot groups A and B are separated, that is, each dot of the reflection image "a" generated by the reflection in the first surface M1 does not overlap with each dot of the reflection image b generated by the reflection in the second surface M2 is g>0. When this situation is described for the relation in FIG. 3, the positional relation of the transparent flat plate 3, the pattern member 4, and the camera 2 and the size of each dot of the pattern X are determined such that the length P of each dot is smaller than the distance Q (P<Q). For example, when the length P of each dot is to be adjusted, it is sufficient that the setup satisfies the following Formula (3).

$$P < 2t \cdot \cos \phi_1 \cdot \tan \phi_2 \quad (3)$$

Here, the pattern X is not limited to dots, and the length P in the direction perpendicular to the direction of extending of the pattern X may appropriately be set up within a range that the above-mentioned condition is satisfied.

Figure 4:
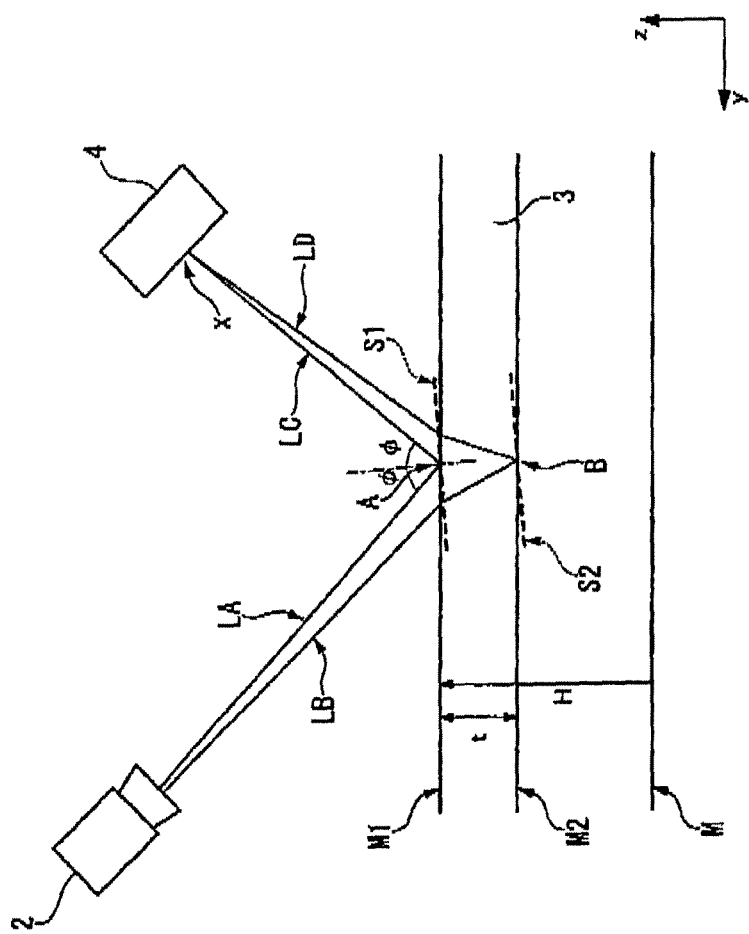
FIG. 4 is a diagram showing a relation between a reflection spot group A and the shape of a first surface M1 of a transparent flat plate 3 according to a first embodiment.

FIG. 4 is a diagram showing the relation between the reflection spot group A and the shape of the first surface M1 of the transparent flat plate 3, and shows a situation that the positional relation of the individual components in FIG. 1 is viewed from the horizontal direction (the x-direction). A method of calculating the shape of the first surface M1 of the transparent flat plate 3 on the basis of the image G is described below with reference to FIGS. 2 and 4.

In FIG. 4, the reflection spot group A is located on the first surface M1 of the transparent flat plate 3. Then, its position (the position in the right and left directions in the figure) can be know from the position (the position in the y-direction in FIG. 2) of the reflection image "a" generated by the reflection spot group A in the image G (FIG. 2).

That is, when a particular image G containing the reflection image "a" is obtained, the reflection spot group A on the first surface M1 of the transparent flat plate 3 is located on the line of sight (the straight line LA in FIG. 4) viewed from the camera 2 toward the direction of the reflection image "a" in the image G. Thus, the position where the line of sight (the straight line LA) intersects the first surface M1 of the transparent flat plate 3 indicates the position of the reflection spot group A on the first surface M1 of the transparent flat plate 3. When it is assumed that the height H measured from a particular reference plane M (the floor or the like) to the first surface M1 of the transparent flat plate 3 is constant, the position of the reflection spot group A on the first surface M1 of the transparent flat plate 3 can be identified in the above-mentioned method.

Here, as shown in FIG. 2, the image G contains: the line of the reflection image "a" generated by the reflection spot group A in the first surface M1 of the transparent flat plate 3; and the line of the reflection image b generated by the reflection spot group B in the second surface M2 of the transparent flat plate 3. Then, as described above, on the basis of the positional relation of the individual components shown in FIG. 1, the upper line (on the negative y-axis direction side in FIG. 2) in the two lines in the image G is the line corresponding to the reflection image "a".

Then, when the position of the reflection spot group A on the first surface M1 of the transparent flat plate 3 has been identified as described above, on the basis of the positional relation of the pattern X, the camera 2, and the reflection spot group A in FIG. 4, the shape of the part at the reflection spot group A within the first surface M1 of the transparent flat plate 3 can be calculated as described below.

That is, as shown in FIG. 4, light (indicated by a straight line LC) emitted from the pattern X of the pattern member 4 is reflected in the first surface M1 of the transparent flat plate 3 at the position of the reflection spot group A, and then travels toward the camera 2. The optical path of the reflected light is a straight line LA. Here, when the position of the reflection spot group A on the first surface M1 of the transparent flat plate 3 is determined, the incident light LC and the reflected light LA are determined. Further, from the condition that the incident angle φ of the incident light LC incident at the position of the reflection spot group A is equal to the reflection angle φ of the reflected light LA reflected at the position of the reflection spot group A, a reflection plane S1 is determined at the position of the reflection spot group A.

The reflection plane S1 is a minute plane constituting the first surface M1 of the transparent flat plate 3 at the position of the reflection spot group A. In other words, the local surface of the transparent flat plate 3 at the position of the reflection spot group A has the same inclination angle as the reflection plane S1 in FIG. 4. As such, the shape (the inclination angle) of the first surface M1 of the transparent flat plate 3 has been obtained at the position of the reflection spot group A.

When similar processing is performed on each spot in the reflection image "a" generated by the reflection spot group A in FIG. 2, the shape of the first surface M1 of the transparent flat plate 3 is obtained at the position of each spot on the reflection spot group A. Further, when similar processing is performed successively in association with the conveyance of the transparent flat plate 3 toward the y-direction, the shape of the entire surface of the first surface M1 of the transparent flat plate 3 can be obtained.

Figure 5:
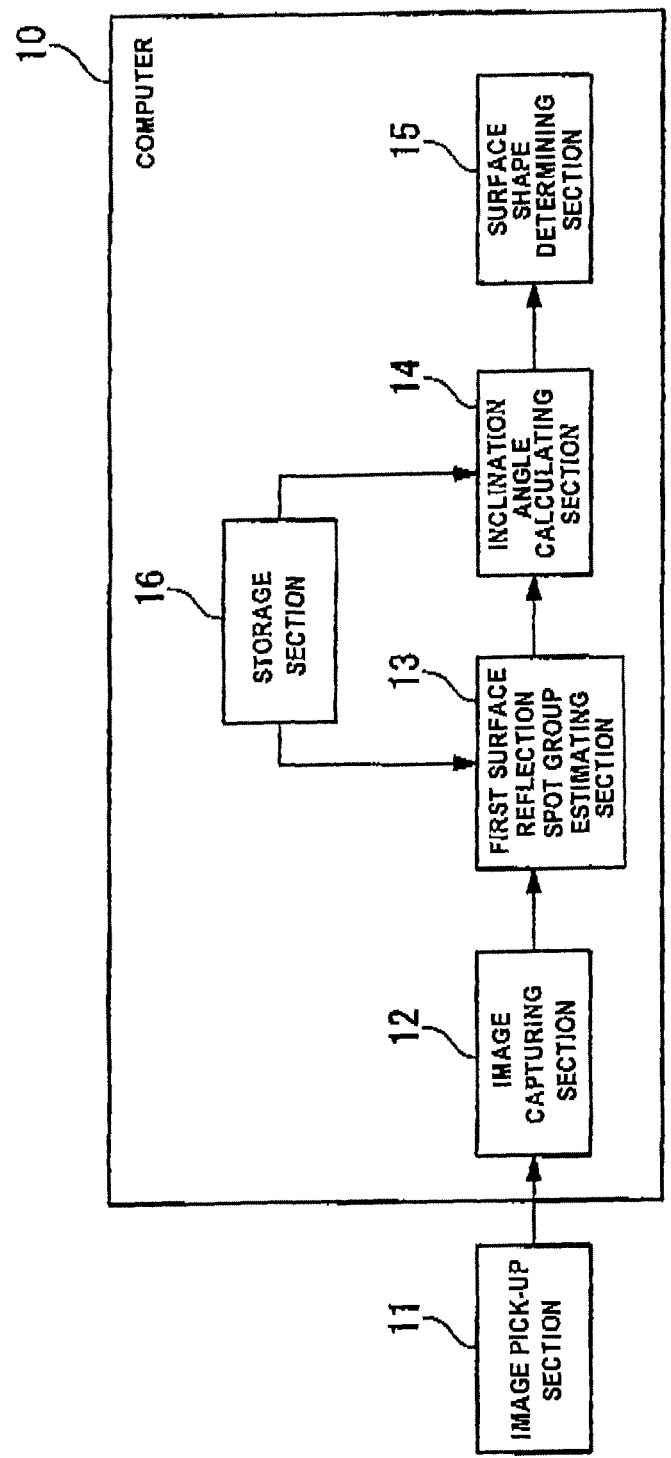
FIG. 5 is a diagram showing a configuration of a shape measuring apparatus for implementing a measuring method for the surface shape of a transparent flat plate according to a first embodiment.

FIG. 5 is a diagram showing the configuration of a shape measuring apparatus for implementing a measuring method for the surface shape of a transparent flat plate according to the above-mentioned embodiment.

In FIG. 5, the shape measuring apparatus includes an image pick-up section 11 and a computer 10. The image pick-up section 11 is the camera 2 shown in the above-mentioned FIGS. 1 and 4. The computer 10 includes an image capturing section 12, a first surface reflection spot group estimating section 13, an inclination angle calculating section 19, a surface shape determining section 15, and a storage section 16. Here, as for the individual sections 12 to 15 of the computer 10 except for the storage section 16, their functions are implemented when a CPU executes a predetermined computer program stored in a ROM or the like.

The image capturing section 12 captures an image G (FIG. 2) from the image pick-up section 11. A single image G may be used. Alternatively, a plurality of images G may be used that are captured successively in correspondence to the conveyance of the transparent flat plate 3. From a single image G, as a result of the processing of the individual sections described below, the shape of the first surface M1 of the transparent flat plate 3 can be obtained in a particular cross section parallel to the x-axis (FIG. 1). Further, when a plurality of consecutive images G are used, the surface shape can be obtained in a somewhat spread region of the first surface M1 of the transparent flat plate 3.

The first surface reflection spot group estimating section 13 detects from the image G a reflection image "a" contained in the image G and generated by the reflection spot group A of the pattern X in the first surface M1 of the transparent flat plate 3. Specifically, first, the first surface reflection spot group estimating section 13 detects a reflection image "a" and a reflection image b (two lines) from the image G by using a widely known image processing technique such as image recognition. As described above, which one of the two lines is the reflection image "a" is determined depending on the positional relation of the transparent flat plate 3, the pattern member 4, and the camera 2, and hence is known. The storage section 16 already stores the known information that indicates which one is the reflection image "a". Then, by using the information, the first surface reflection spot group estimating section 13 detects the reflection image "a" from the detected two lines consisting of the reflection image "a" and the reflection image b.

On the basis of the reflection image "a" detected from the image G, the inclination angle calculating section 14 calculates the inclination angle of the first surface M1 of the transparent flat plate 3 at the position of the reflection spot group A on the first surface M1 of the transparent flat plate 3. The detailed calculation procedure is as follows.

First, the inclination angle calculating section 14 calculates the vertical direction (y-direction) position of the reflection image "a" in the image G. Then, on the basis of the vertical direction position, the inclination angle calculating section 14 calculates the position of the reflection spot group A located on the first surface M1 of the transparent flat plate 3. In order that the position of the reflection spot group A on the first surface M1 is obtained, as described above, it is sufficient that the position where the straight line LA in FIG. 4 intersects the first surface M1 of the transparent flat plate 3 is obtained by geometric calculation. Alternatively, the correspondence relation between the vertical direction position in the image G and the position on the first surface M1 of the transparent flat plate 3 may be tabulated in advance on the basis of the relative arrangement of the camera 2 and the transparent flat plate 3. Then, by using the table, the position on the first surface M1 of the transparent flat plate 3 may be calculated on the basis of the vertical direction position in the image G. The information concerning the arrangement of the camera 2, the above-mentioned table, and the like necessary for the above-mentioned geometric calculation are stored in the storage section 16. Then, using these, the inclination angle calculating section 14 performs the above-mentioned processing.

Then, the inclination angle calculating section 14 calculates the individual optical paths (see FIG. 4) of the incident light LC from the pattern X and the reflected light LA toward the camera 2 at the position of the reflection spot group A on the first surface M1 of the transparent flat plate 3 obtained as described above. Then, the inclination angle calculating section 14 calculates the reflection plane S1 that reflects the incident light LC in the direction of the reflected light LA (a reflection plane that satisfies the relation that the reflection angle φ of the incident angle φ=the reflected light LA of the incident light LC) (see FIG. 4), and then calculates the inclination angle of the obtained reflection plane S1. This inclination angle is the inclination angle of the first surface M1 of the transparent flat plate 3 at the position of the reflection spot group A on the first surface M1 of the transparent flat plate 3, and is the calculation result of the inclination angle calculating section 14.

Here, in order to calculate respectively the incident light LC, the reflected light LA, and the reflection plane S1, it is sufficient that geometric calculation is performed by using the positional relation of the individual components shown in FIG. 4. Alternatively, the correspondence relation between the position of the reflection spot group A on the first surface M1 of the transparent flat plate 3 and the inclination angle of the reflection plane S1 may be tabulated in advance on the basis of the relative arrangement between the three components consisting of the camera 2, the transparent flat plate 3, and the pattern member 4 (the pattern X). Then, the individual results may be calculated by using the table. The information concerning the arrangement of the camera 2, the above-mentioned table, and the like necessary for the above-mentioned geometric calculation are stored in the storage section 16. Then, using these, the inclination angle calculating section 14 performs the above-mentioned processing.

The inclination angle calculating section 14 performs the processing consisting of these individual calculation procedures, onto each spot of the reflection spot group A (e.g., onto the reflection spots corresponding to all dots constituting the pattern X).

On the basis of the inclination angle of the first surface M1 of the transparent flat plate 3 obtained by the inclination angle calculating section 14, the surface shape determining section 15 determines the shape of the first surface M1 of the transparent flat plate 3. When a single image G captured by the image capturing section 12 is used alone, the shape of the first surface M1 of the transparent flat plate 3 is determined in one cross section parallel to the x-axis (FIG. 1). Alternatively, a plurality of images G are used that are captured successively in correspondence to the conveyance of the transparent flat plate 3, the shape is determined in a somewhat spread region in the first surface M1 of the transparent flat plate 3. For example, when this shape measurement is performed continuously at all times, waviness and the like in the first surface of the glass ribbon 204 shown in FIG. 10 can be monitored over the entirety in the length direction of the glass ribbon.

Second Embodiment

A second embodiment of the present invention is described below with reference to the drawings. Here, the second embodiment is the same as the first embodiment except for the points described below.

FIG. 6 is a diagram showing a pattern provided in a pattern member 4' and an image G' captured by the camera 2.

The pattern member 4' includes three rows of patterns X(1), X(2), X(3) where a large number of dots are aligned in line in one direction (the right and left directions in the figure). When the pattern member 4' like this is used, the image G' contains six lines in total consisting of: reflection images a(1), a(2), a(3) of the reflection spot group A of the individual patterns X(1), X(2), X(3) generated by the first surface M1 of the transparent flat plate 3; and reflection images b(1), b(2), b(3) of the reflection spot group B of the individual patterns X(1), X(2), X(3) generated by the second surface M2 of the transparent flat plate 3. When the intervals of the pattern X of the three rows (1), X(2), X(3) are set up appropriately, the individual reflection images can be separated within the image G'. Further, which one of these six lines is the reflection image of a particular pattern (for example, the pattern X (1)) generated by the first surface M1 of the transparent flat plate 3 can be known, similarly to the first embodiment, from the positional relation of the individual components shown in FIG. 1.

According to the present configuration, even when a particular reflection image in the image G' becomes indistinct, for example, by a reason that dust adheres to the first surface M1 of the transparent flat plate 3, the shape of the first surface M1 of the transparent flat plate 3 can be measured by using other clear reflection images.

Third Embodiment

A third embodiment of the present invention is described below with reference to the drawings. Here, the third embodiment is the same as the first embodiment except for the points described below.

In the first embodiment, the height H measured from the reference plane M to the first surface M1 of the transparent flat plate 3 has been known. In contrast, in the third embodiment, the shape of the first surface M1 of the transparent flat plate 3 can be measured even when the height H of the first surface M1 of the transparent flat plate 3 is unknown.

Figure 7:
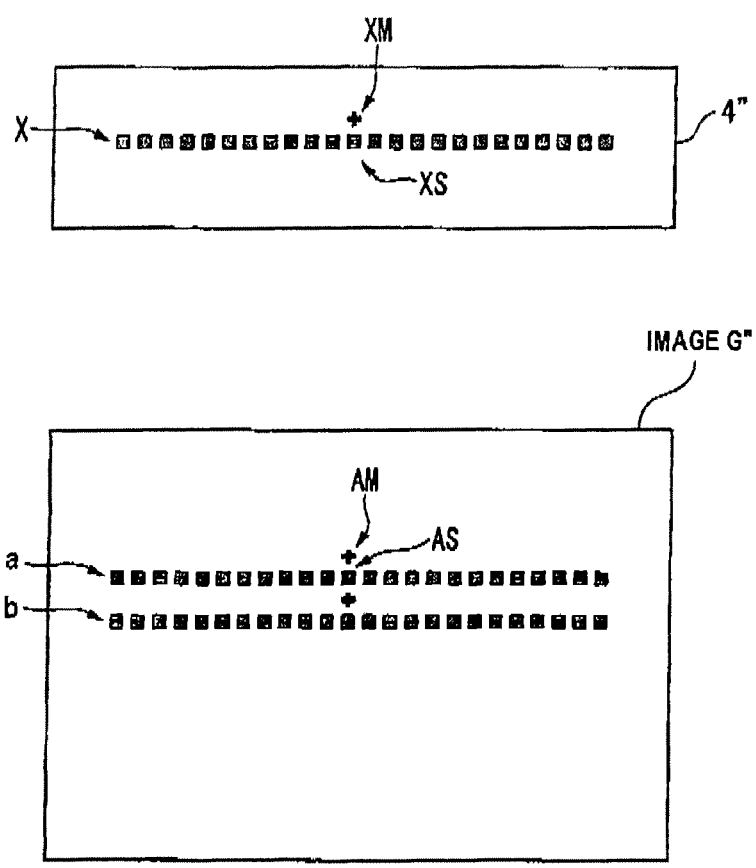
FIG. 7 is a diagram showing a pattern provided in a pattern member 4" and an image G" captured by a camera 2 according to a third embodiment.

FIG. 7 is a diagram showing a pattern provided in a pattern member 4" and an image G" captured by the camera 2.

The pattern member 4" includes: a pattern X where a large number of dots are aligned in line in one direction (the right and left directions in the figure); and a marker XM arranged near one dot XS constituting the pattern X. When the pattern member 4" like this is employed, in the image G" contains a reflection image of the marker XM, in addition to the reflection images "a" and b of the reflection spot group A and the reflection spot group B of the pattern X generated by the first surface M1 and the second surface M2 of the transparent flat plate 3.

In the present embodiment, the unknown height H of the first surface M1 of the transparent flat plate 3 is obtained by using the reflection images of the marker XM and the dot XS. Once the height H of the first surface M1 of the transparent flat plate 3 is obtained, similarly to the first embodiment, the shape of the first surface M1 of the transparent flat plate 3 is obtained by using the reflection image of the pattern X.

A method of obtaining the height H of the first surface M1 of the transparent flat plate 3 by using the reflection images of the marker XM and the dot XS is described below with reference to FIGS. 8 and 9.

First, attention is focused on the dot XS. Light emitted from the dot XS (see FIG. 8) on the pattern member 4" is reflected in the first surface M1 of the transparent flat plate 3 and thereby forms reflection image AS (see FIG. 7) in the image G". At that time, since the height H of the first surface M1 of the transparent flat plate 3 is unknown, the true reflection spot on the first surface M1 of the transparent flat plate 3 is not uniquely identified (the reflection spot is located somewhere on a straight line LS extending from the camera 2 toward the reflection image AS in the image G"). FIG. 8 shows three reflection spot candidates $A_1(1), A_1(2), A_1(3)$ having different height H values. The height values of the reflection spot groups $A_1(1)$, $A_1(2)$, and $A_1(3)$ are denoted by $H_1$, $H_2$, $H_3$ ($H_1<H_2<H_3$) respectively.

Here, when the reflection spot group $A_1(1)$ of height $H_1$ is adopted, the (assumed) tangential plane of the transparent flat plate 3 in the reflection spot group $A_1(1)$ is expected to have an inclination angle $\theta_1(1)$ equal to that of the reflection plane $S_1$ where the light emitted from the dot XS on the pattern member 4" and then incident on the reflection spot group $A_1(1)$ is reflected toward the camera 2 along the straight line LS. When the reflection spot group $A_1(2)$ or $A_1(3)$ is adopted, similarly, the (assumed) tangential plane of the transparent flat plate 3 at each reflection spot has an inclination angle $\theta_1(2)$ or $\theta_1(3)$ equal to that of the corresponding reflection plane $S_2$ or $S_3$.

At that time, when the reflection spot is located at a higher position (that is, $A_1(2)$ is higher than $A_1(1)$, and $A_1(3)$ than $A_1(2)$), the incident angles from the dot XS on the pattern member 4" toward the individual reflection planes $S_1$, $S_2$, $S_3$ become shallower. Thus, the relation of $\theta_1(1)<\theta_1(2)<\theta_1(3)$ is realized (here, the inclination angle is defined as the angle contained by the negative x-axis direction in the figure and the normal of each reflection plane directed upward in the figure). This relation is shown by a curve $C_1$ in the graph of FIG. 9. As such, the inclination angle $\theta_1(n)$ is a function of the height $H_n$ of the reflection spot. Here, as described above, which point on the curve $C_1$ corresponds to the true reflection spot cannot uniquely be determined.

Next, attention is focused on the marker XM. Similarly to the dot XS, the reflection spot on the first surface M1 of the transparent flat plate 3 where the light emitted from the marker XM on the pattern member 4" is reflected toward the camera 2 is located somewhere on the straight line LM directed from the camera 2 toward the reflection image AM in the image G" (not uniquely identified).

Next, attention is focused on intersection point groups $A_2(1), A_2(2), A_2(3), \ldots$ where the above-mentioned (assumed) tangential planes (the reflection planes $S_1$, $S_2$, $S_3, \ldots$) that pass respectively the above-mentioned reflection spot candidates $A_1(1), A_1(2), A_1(3), \ldots$ intersect the straight line LM. The dot XS and the marker XM are neighborhood points on the pattern member 4". Thus, each spot group $A_1(n)$ and the corresponding spot group $A_2(n)$ are similarly neighborhood points ($n=1, 2, \ldots$).

Here, a premise is placed that the change in the shape of the first surface M1 of the transparent flat plate 3 is sufficiently loose. Then, at two mutual neighborhood points on the first surface M1 of the transparent flat plate 3, the individual tangential planes passing these two points respectively can be regarded as the same plane.

Thus, if a particular spot group $A_1(k)$ among the above-mentioned reflection spot candidates is the true reflection spot on the first surface M1 of the transparent flat plate 3, the spot group $A_2(k)$ located on the tangential plane (the reflection plane $S_k$) of the transparent flat plate 3 that passes the spot group $A_1(k)$ is concluded to be similarly a point on the first surface M1 of the transparent flat plate 3. Then, when a reflection plane $S_k'$ is considered that, by using the spot group $A_2(k)$ as a reflection spot, reflects the light from the upper the marker XM on the pattern member 4" toward the direction of the camera 2 along the straight line LM, the reflection plane (that is, the tangential plane of the transparent flat plate 3 in the spot group $A_2(k)$) becomes identical to the tangential plane (the reflection plane $S_k$) of the transparent flat plate 3 in the spot group $A_1(k)$. Thus, the inclination angle $\theta_2(k)$ is concluded to be equal to the inclination angle $\theta_1(k)$. FIG. 8 shows a situation that the spot group $A_1(2)$ is the true reflection spot on the first surface M1 of the transparent flat plate 3.

Figure 8:
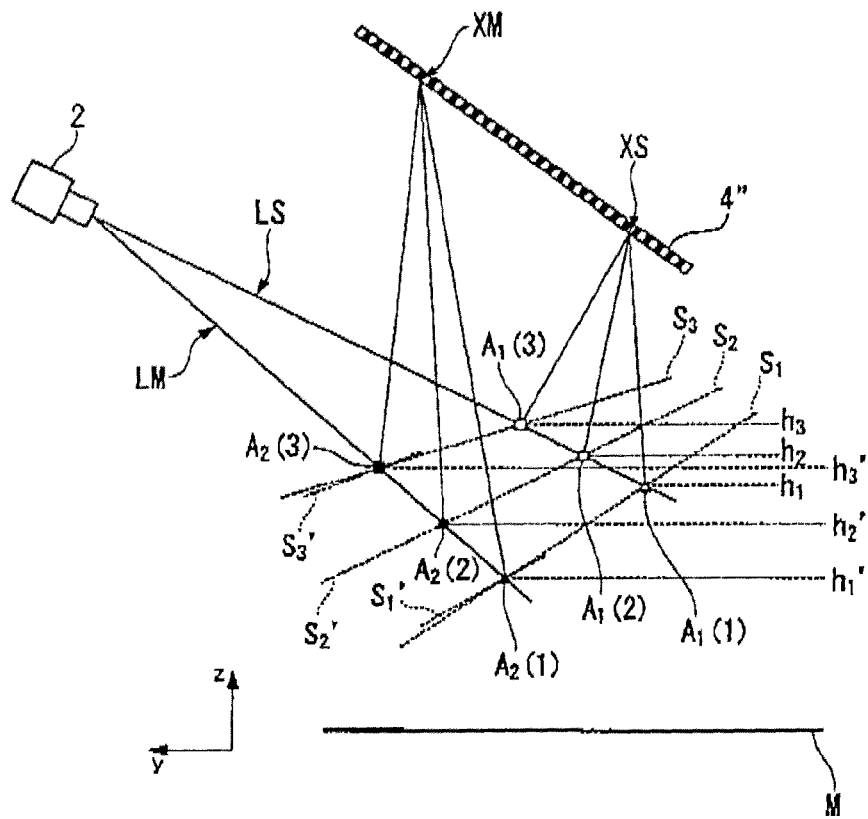
FIG. 8 is a diagram showing a method of obtaining the height H of a transparent flat plate 3 first surface according to a third embodiment.
Figure 9:
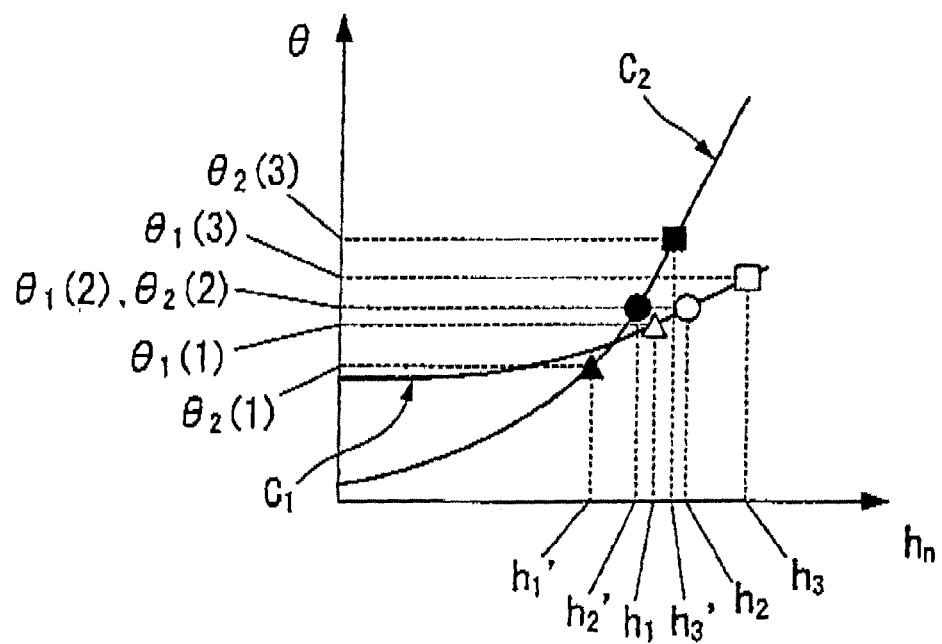
FIG. 9 is a diagram showing a method of obtaining the height H of a transparent flat plate 3 first surface according to a third embodiment.

On the other hand, as for spot groups $A_1(j)$ (here, and corresponding to the spot groups $A_1(1)$ and $A_1(3)$ in FIG. 8) which is not the true reflection spot on the first surface M1 of the transparent flat plate 3, the spot group $A_2(j)$ located on the (assumed) tangential plane (the reflection plane $S_j$) of the transparent flat plate 3 that passes the spot group $A_1(j)$ is not a point on the first surface M1 of the transparent flat plate 3. Thus, the inclination angle $\theta_2(j)$ of the reflection plane where the light from the upper the marker XM on the pattern member 4" is reflected at the spot group $A_2(j)$ toward the direction of the camera 2 along the straight line LM is concluded to be different from the inclination angle $\theta_1(j)$.

Thus, as for the above-mentioned intersection point groups $A_2(1), A_2(2), A_2(3), \ldots$ between the individual (assumed) tangential planes (the reflection planes $S_1, S_2, S_3, \ldots$) passing the reflection spot candidates $A_1(1), A_1(2), A_1(3), \ldots$ corresponding to the dot XS and the straight line LM determined by the marker XM, the inclination angles $\theta_2(1), \theta_2(2), \theta_2(3), \ldots$ of the (assumed) tangential planes (the reflection planes $S_1', S_2', S_3', \ldots$) are acquired. Then, by acquiring a reflection spot candidate $A_1(k)$ satisfying $\theta_2(k)=\theta_1(k)$, it is concluded that the inclination angle $\theta_1(k)$ and the height $H_k$ at the reflection spot are obtained because the reflection spot group $A_1(k)$ is the true reflection spot.

In addition to the curve $C_1$ described above, the graph of FIG. 9 shows a curve $C_2$ indicating the relation between the height $H'_n$ of each above-mentioned intersection point group $A_2(n)$ and the inclination angle $\theta_2(n)$ of the tangential plane at each intersection point group $A_2(n)$. In this graph, the spot group $A_1(2)$ where the value $\theta_1(n)$ agrees with the value $\theta_2(n)$ is the true reflection spot on the first surface M1 of the transparent flat plate 3.

As described above, the height $H=H_k$ of the first surface M1 of the transparent flat plate 3 has been calculated. Thus, similarly to the first embodiment, the shape of the first surface M1 of the transparent flat plate 3 can be obtained by using the height H.

Fourth Embodiment

Figure 11:
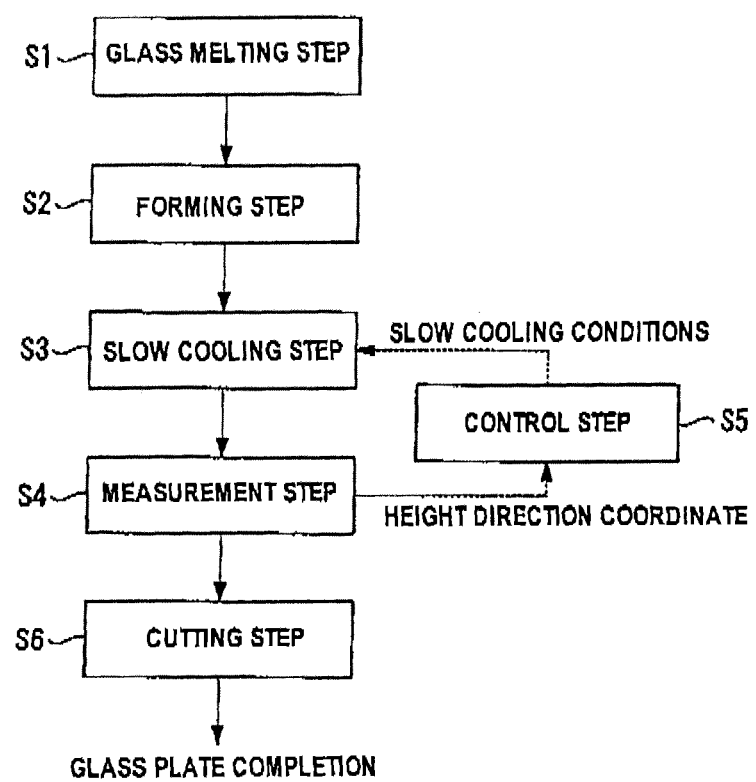
FIG. 11 is a flow chart showing the steps of a manufacturing method for glass plates.

An example of application of the present invention in a manufacturing line for glass plates is described below. FIG. 10 is a schematic explanation diagram of a manufacturing line for glass plates to which the shape measuring apparatus shown in FIG. 5 is applied. A manufacturing method for glass plates in the manufacturing line shown in FIG. 10 includes: a melting step of melting glass raw material so as to obtain molten glass; a forming step of forming the molten glass into a continuous plate-shaped glass ribbon; a slow cooling step of gradually cooling the glass ribbon in the course of moving; a shape measurement step of measuring the surface shape of the glass ribbon; a cutting step of cutting the glass ribbon; a control stop of, on the basis of the surface shape of the glass ribbon obtained by the measurement step, controlling slow cooling conditions in the slow cooling step. FIG. 11 shows the steps of the manufacturing method for glass plates.

Specifically, during the manufacturing steps for glass plates, when a glass ribbon has been concluded to have a large warp on the basis of the data of surface shape of the glass ribbon obtained in the shape measuring method of the present invention, slow cooling conditions in the slow cooling step, like cooling rate conditions and cooling temperature conditions, are changed with taking into consideration the magnitude and the location of the warp. This prevents a defect in the shape caused by the warp or a crack caused by the warp, and thereby permits manufacturing of glass plates at a satisfactory yield.

Examples of the forming step include a float method, a roll-out method, a down draw method, and a fusion method. The present invention may appropriately employ any one of these, or another method. The example in FIG. 10 is described for a case that a float method is employed.

At the melting step (S1 in FIG. 11), a batch obtained by preparing and mixing raw materials such as silica sand, limestone, and soda ash in accordance with the composition of the glassware is supplied into a furnace, and then heated and melted at a temperature of approximately 1400° C. or higher in accordance with the type of the glass, so that molten glass is obtained. For example, the batch is supplied into the furnace through one end of the furnace. Then, a flame obtained by combustion of heavy oil or a flame obtained by combustion of mixture of natural gas and air is applied on the batch, so that the batch is heated and melted at a temperature of approximately 1550° C. or higher. As a result, molten glass is obtained. Further, an electric melting furnace may be employed for obtaining molten glass.

At the forming step (S2 in FIG. 11), the molten glass obtained at the melting step is introduced through a furnace downstream section 201 into a molten tin bath 203. Then, the molten glass is floated on the molten tin 202 and moved in the conveyance direction in the figure, so as to be formed into a continuous plate-shaped glass ribbon 204 (corresponding to the transparent flat plate 3). At that time, in order that the glass ribbon 204 should be formed in a predetermined plate thickness, revolving rolls (top roll 205) are pressed against both side parts of the glass ribbon 204 so that the glass ribbon 204 is expanded outward in the width direction (a direction perpendicular to the conveyance direction).

At the slow cooling step (S3 in FIG. 11), the glass ribbon 204 formed as described above is extracted from the molten tin bath 203 by lift-out rolls 208. Then, the glass ribbon 204 is moved inside the lehr 210 in the conveyance direction in the figure by metallic rolls 209, so that the temperature of the glass ribbon 204 is cooled gradually. Subsequently, in the course from the exit of the lehr 210 to the cutting step, the glass ribbon 204 is cooled further into a temperature near the ordinary temperature. The lehr 210 includes a mechanism for supplying a controlled amount of heat by using combustion gas or an electric heater so as to perform slow cooling, which is located at a necessary position in the furnace. The temperature of the glass ribbon 204 at the exit from the lehr 210 is at or below the strain point of the glass of the glass ribbon 204. That is, depending on the type of glass, the glass ribbon 204 is usually cooled to 150 to 250° C. The slow cooling step is employed for the purpose of removing the residual stress in the inside of the glass ribbon 209 and of reducing the temperature of the glass ribbon 204. At the slow cooling step, the glass ribbon 204 passes through a measurement section 211 (corresponding to the shape measuring apparatus in FIG. 5), and is then conveyed to a glass ribbon cutting section 212. The glass ribbon cutting section 212 cuts the glass ribbon 204 having undergone slow cooling into a temperature near the ordinary temperature (the cutting step). Here, the temperature of the glass ribbon at the glass ribbon cutting section 212 is usually in the range of an ambient temperature at the place to 50° C.

The position of image capturing for the glass ribbon 204 at the measurement step (S4 in FIG. 11) (that is, the position of the measurement section 211) is a position where the temperature of the glass ribbon 204 is at or below the strain point of the glass. Usually, the measurement section 211 is arranged at a position in the downstream of the conveyance direction relative to the glass ribbon exit of the lehr 210. Further, it is preferable that the measurement section 211 is arranged at a position where the temperature of the glass ribbon 204 is at or below 200° C. Further, the measurement section 211 may be provided in the immediate upstream of the cutting step. However, in a case that the data obtained at the measurement step is to be reflected at the cutting step, it is preferable that the measurement section 211 is arranged at a position distant from the cutting position by 30 cm or greater, in particular, by 1 m or greater, depending on the movement speed of the glass ribbon 204.

At the control step (S5 in FIG. 11), controlling means (not shown) is utilized that, on the basis of the surface shape of the glass ribbon 204 obtained at the measurement step, calculates slow cooling conditions used in the lehr 210. In response to instructions of the slow cooling conditions exchanged with the lehr 210, the controlling means changes the conditions for the combustion gas, the electric heater, and the like provided in the lehr 210. As such, the energy provided partly to the glass ribbon 204 or the rate of the provided energy is changed so that control can be performed for suppressing deformation such as curvature.

The embodiments of the present invention have been described above in detail with reference to the drawings. However, detailed configuration is not limited to these embodiments, and may adopt a design and the like within a scope not departing from the spirit of the present invention.

The present application has been described in detail with reference to particular embodiments. However, it is obvious for the person skilled in the art that various kinds of changes and modifications can be made without departing from the spirit and the scope of the present invention. The present application is based on a Japanese patent application (Japanese Patent Application No. 2010-136510) filed on Jun. 15, 2010, whose contents are incorporated herein by reference.

EXPLANATION OF REFERENCE NUMERALS

2 . . . camera
3 . . . transparent flat plate
4 . . . pattern member
X . . . pattern
M1 . . . first surface of transparent flat plate 3
M2 . . . second surface of transparent flat plate 3
A . . . reflection spot group of pattern X generated by first surface M1 of transparent flat plate 3
a . . . reflection image generated by reflection spot group A within image
B . . . reflection spot group of pattern X generated by second surface M2 of transparent flat plate 3
b . . . reflection image generated by reflection spot group B within image
R . . . image pick-up area of camera 2
M . . . reference plane
S1, S2 . . . reflection plane
10 . . . computer
11 . . . image pick-up section
12 . . . image capturing section
13 . . . first surface reflection spot group estimating section
14 . . . inclination angle calculating section
15 . . . surface shape determining section 16 . . . storage section

The invention claimed is:

1. A shape measuring method comprising the steps of:
by using an image pick-up section arranged such that an optical axis becomes perpendicular to a direction of extending of a linear pattern arranged above a transparent flat plate serving as a measurement object, capturing an image of two reflection spot groups of the pattern generated by a first surface and a second surface of the transparent flat plate and thereby generates an image containing two reflection images separated in a direction perpendicular to the direction of extending;
estimating from the image a first surface reflection spot group of the pattern in the first surface of the transparent flat plate by using a positional relation of the transparent flat plate, the pattern, and the image pick-up section;
calculating an inclination angle of the first surface of the transparent flat plate at a position of the estimated first surface reflection spot group by using the positional relation of the transparent flat plate, the pattern, and the image pick-up section; and
determining a shape of the first surface of the transparent flat plate based on the calculated inclination angle.

2. The shape measuring method according to claim 1, wherein
the inclination angle calculating step calculates the inclination angle based on a condition that an incident angle of incident light travelling from the pattern toward the first surface reflection spot group is equal to a reflection angle of reflected light travelling from a position of the first surface reflection spot group toward the image pick-up section.

3. The shape measuring method according to claim 1, wherein
the pattern is a pattern constructed such that a plurality of dots are arranged linearly in the extending direction.

4. The shape measuring method according to claim 1, wherein
the transparent flat plate is conveyed in a direction perpendicular to the direction of extending.

5. A manufacturing method for glass plates comprising:
a melting step of melting raw material so as to obtain molten glass;
a forming step of forming the molten glass into a continuous plate-shaped glass ribbon;
a slow cooling step of gradually cooling the glass ribbon in the course of conveying so as to remove stress;
a measurement step of measuring the surface shape of the glass ribbon;
a cutting step of cutting the glass ribbon; and
a control step of controlling slow cooling conditions in the slow cooling step based on a measurement result of the measurement step, wherein
the measurement step is a step in which measurement is performed on the glass ribbon by using the shape measuring method according to claim 1.

6. A manufacturing method for glass plates comprising:
a melting step of melting raw material so as to obtain molten glass;
a forming step of forming the molten glass into a continuous plate-shaped glass ribbon;
a slow cooling step of gradually cooling the glass ribbon in the course of conveying so as to remove stress;
a measurement step of measuring the surface shape of the glass ribbon;
a cutting step of cutting the glass ribbon; and
a control step of controlling slow cooling conditions in the slow cooling step based on a measurement result of the measurement step, wherein
the measurement step is a step in which measurement is performed on the glass ribbon by using the shape measuring method according to claim 2.

7. A manufacturing method for glass plates comprising:
a melting step of melting raw material so as to obtain molten glass;
a forming step of forming the molten glass into a continuous plate-shaped glass ribbon;
a slow cooling step of gradually cooling the glass ribbon in the course of conveying so as to remove stress;
a measurement step of measuring the surface shape of the glass ribbon;
a cutting step of cutting the glass ribbon; and a control step of controlling slow cooling conditions in the slow cooling step based on a measurement result of the measurement step, wherein the measurement step is a step in which measurement is performed on the glass ribbon by using the shape measuring method according to claim 3.

8. A manufacturing method for glass plates comprising:

a melting step of melting raw material so as to obtain molten glass;

a forming step of forming the molten glass into a continuous plate-shaped glass ribbon;

a slow cooling step of gradually cooling the glass ribbon in the course of conveying so as to remove stress;

a measurement step of measuring the surface shape of the glass ribbon;

a cutting step of cutting the glass ribbon; and a control step of controlling slow cooling conditions in the slow cooling step based on a measurement result of the measurement step, wherein the measurement step is a step in which measurement is performed on the glass ribbon by using the shape measuring method according to claim 4.

\* \* \* \* \*